Figure 1:
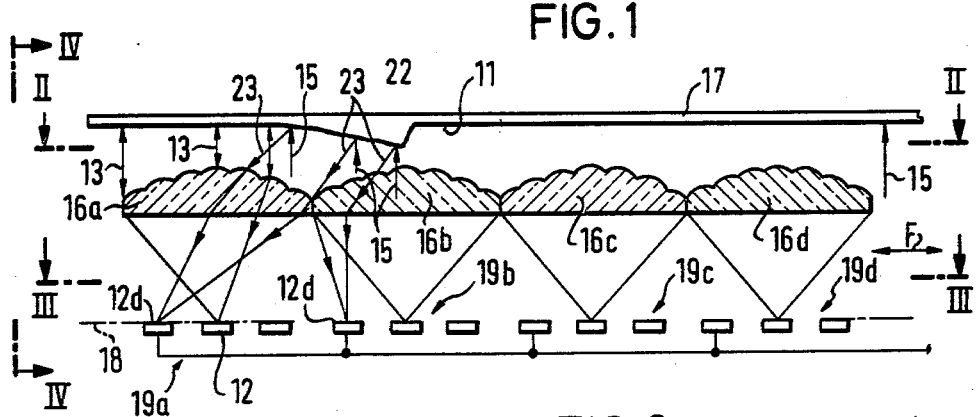

United States Patent [19]

Sick

[11] 4,227,091
[45] Oct. 7, 1980

[54] OPTICAL MONITORING APPARATUS

[75] Inventor: Erwin Sick, Icking, Fed. Rep. of Germany

[73] Assignee: Erwin Sick GmbH, Optik-Elektronik, Waldkirch, Fed. Rep. of Germany

[21] Appl. No.: 12,046

[22] Filed: Feb. 14, 1979

[30] Foreign Application Priority Data

Feb. 27, 1978 [DE] Fed. Rep. of Germany ....... 2808360

[51] Int. Cl.² .................................................. G01N 21/32
[52] U.S. Cl. .................................... 250/572; 356/430
[58] Field of Search ............ 250/216, 562, 563, 571, 250/572, 566; 356/445, 448, 429, 430; 350/211

[56] References Cited
U.S. PATENT DOCUMENTS

| | | | |
|---|---|---|---|
| 3,756,725 | 9/1973 | Manring | 356/448 |
| 3,800,148 | 3/1974 | DeCock | 250/572 |
| 3,812,348 | 5/1974 | Lippke | 356/430 |

Primary Examiner—David C. Nelms

[57] ABSTRACT

Optical monitoring apparatus for detecting the angles at which light rays leave a material surface scanned by a light bead such as an incident laser beam includes a row of individual Fresnel lenses arranged edgewise directly adjacent each other to focus light leaving the surface onto respective arrays of photodetectors arranged in their focal planes.

The outputs from the photodetectors are connected together by processing means to allow evaluation of their output signals. The row of Fresnel lenses may also be used for other optical monitoring purposes.

7 Claims, 4 Drawing Figures

OPTICAL MONITORING APPARATUS

The present invention relates to optical monitoring apparatus and has particular reference to an apparatus for the separate detection of light rays which leave a surface scanned by a light bead at various angles.

It is already known (DE-OS No. 21 15 979) e.g. in connection with moving paper or material webs which are to be monitored for faults, to continuously scan such webs transversely of their direction of movement by a light ray originating from a laser. A light bead thus moves over the web from which, depending on the nature of the surface or the location of faults, light is reflected in various directions. The light leaving the light bead is reflected through a spatial angle in such a way that the intensity of the light rays in the individual directions is in total characteristic of the condition of the surface. It is already known that the receiving devices which monitor the light bead, and which mostly include a light conducting rod extending parallel to the scanning direction and also a cylindrical lens arranged before the light conducting rod, can be arranged at various angles in order to provide the most favourable conditions for detection. In general, the light intensity received by the detection device will be largest in the direction of specular reflection and will decrease to a greater or lesser extent at angles which deviate from the angle of specular reflection.

The disadvantage of all the known detection devices for such scanning light beads resides in the fact that the detection is mostly restricted to a single or at most two directions relative to the surface.

The same disadvantage also applies to a device for examining and sorting strip- or leaf-like products (DE-OS No. 1 573 396). In this case light conductors are united together into surface-like form with its end face arranged in the vicinity of the web or track to be monitored. A special light conducting device must be provided for each angle at which it is intended to detect light. This is not only expensive and troublesome but also limits the number of angular ranges that can be recognized.

An optical apparatus for detection of the light exit angle is also already known (DE-OS No. 25 32 603) in which a stepped mirror arrangement deflects the light leaving a surface at various angles onto an arrangement of individual photodetectors and, indeed, such that a particular individual photodetector always only detects the light from a narrowly defined angular range.

The known apparatus is, indeed, relatively simply constructed by reason of the use e.g. of a stepped mirror arrangement arranged on the light conducting rod and only a single group of photodetectors. The manufacture of stepped mirror arrangements and in particular light conducting rods is, however, associated with a certain degree of trouble and expense to satisfy the quality requirements that are necessary.

It is thus a principal object of the present invention to provide an apparatus of the kind previously named by means of which, on the one hand, the various angles at which light rays leave the surface can be very exactly determined but which, on the other hand, can be manufactured with little trouble or expense and moreover ensures a compact construction.

According to the present invention there is provided, in the path of the light rays leaving the surface, a strip-like row of Fresnel lenses extending in the scanning direction, said strip-like row comprising a series of individual Fresnel lenses arranged edge-wise directly adjacent one another with at least the adjacent edges of each neighbouring pair of Fresnel lenses being plane and their being further provided a respective group of a plurality of photo-detectors arranged in the focal plane of each individual Fresnel lens and processing means for processing the electrical output signals from said photodetectors.

The row of Fresnel lenses taught by the present invention can however readily be utilised in other optical monitoring apparatus and thus, also according to the present invention, there is provided a plurality of individual Fresnel lenses arranged edgewise directly adjacent each other with at least the adjacent edges of neighbouring pairs of Fresnel lenses being plane.

The Fresnel lenses used in accordance with the invention can be made with very low trouble or cost e.g. as pressed components in a transparent synthetic material without further ado. The Fresnel lenses ensure a very compact construction because the short focal length of the Fresnel lenses makes possible the arrangement of the photodetectors at a small distance from the lens body. Surprisingly, the trouble and expense incurred for the apparatus of the invention is very low although a group of several photodetectors is necessary for each Fresnel lens. Photodetectors are, however, currently so inexpensively available in the form of photodiodes that the additional trouble and expense of providing the larger number of photodetectors in no way exceeds the savings which are achieved by renouncing the light conducting rod with its high optical requirements. It is of particular significance that, by reason of the arrangement of the invention, the accuracy of the association of the rays leaving the surface at a specified angle with the individual photodetectors is significantly improved.

Figure 2:
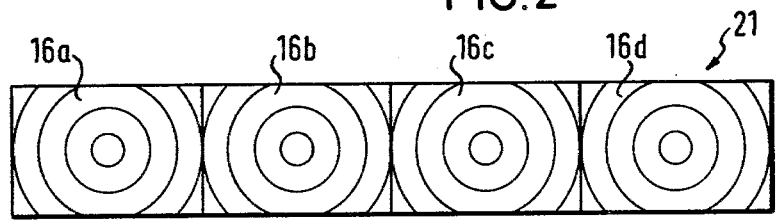
Figure 3:
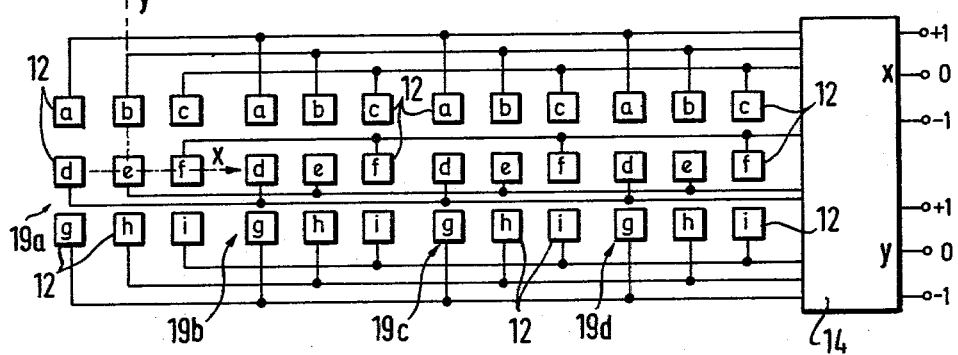

The invention will now be described by way of example only and with reference to the accompanying drawing which shows:

FIG. 1 a schematic side view of an optical apparatus in accordance with the invention for determining the light exit angle;

FIG. 2 a view in the direction of the line II—II;

FIG. 3 a view on the line III—III of FIG. 1 and

Figure 4:
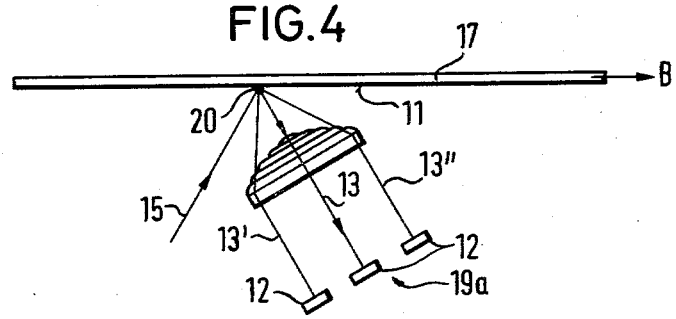

FIG. 4 a view on the line IV—IV of FIG. 1.

In FIGS. 1 to 4 there is shown optical monitoring apparatus for the separate detection of light rays which leave a surface scanned by a light bead in the form of an incident laser beam 15. The laser beam 15 periodically scans the surface, in this case, a material web 17 in the direction of the arrow F of FIG. 1 transversely to its direction of movement B. A light bead 20 thus periodically moves transversely over the surface 11 of the web 17.

A row 21 of individual Fresnel lenses (FIG. 2) is provided in accordance with the invention for detecting the light reflected from the surface 11 and comprises individual Fresnel lenses 16a, b, c, d cut out into rectangles so that the centre of the individual rectangle coincides with the optical centre of the associated Fresnel lens. The individual Fresnel lenses are arranged edgewise directly adjacent one another to produce the strip-like arrangement as seen in FIG. 2 which can receive light over its entire length and which can concentrate the light in the manner described in the following.

In accordance with the invention all the Fresnel lenses 16a, b, c, d have a common focal plane 18 in which the groups 19a, b, c, d of individual photodetectors 12 are arranged in the manner which can be seen in detail from FIGS. 1, 3 and 4. A group 19a, b, c or d of photodetectors 12 is associated with each of the Fresnel lenses 16a, b, c d. These groups are arranged as can be seen from FIG. 3 in the form of an X-Y-coordinate system but can, however, also be grouped together in another system e.g. a polar coordinate system.

In FIG. 3 a total of nine photodetectors 12a, b, c, d, e, f, g, h and i are associated with each Fresnel lens 16 and are grouped in a regular pattern (rectangular form) around a central photodetector 12e located at the focal point.

In accordance with FIG. 3 the respective corresponding photodetectors 12a, b, c, ... to 12i of each group are connected together and are led to processing means including processing electronics 14. The connection together of the individual corresponding photodetectors 12a, b, c, ... preferably takes place in such a fashion that they are applied to the different inputs of an OR-gate.

At the output of the electronic processing circuit three X and three Y signals are then derived by means of which the position of the photodetector on which the light ray is incident is exactly defined.

On the assumption that the surface 11 of the web 17 has directionally reflecting characteristics the laser beam 15 of FIGS. 1 and 4 is so reflected as a light ray 13 that it is deflected through one of the Fresnel lenses 16a, b, c, d respectively onto the central photodetector 12e.

If the surface 11 of the web 17 of FIG. 1 now has a fault 22 which reflects the laser beam 15 at an angle as reflected ray 23 then this reflected ray 23 reaches one of the outer photodetectors because of the imaging characteristics of the Fresnel lenses 16; in the present example it falls on the photodetector 12d. in FIG. 1 the fault 22 is illustrated as being so extended that it stretches over two neighbouring Fresnel lenses 16a and 16b. As can be seen, however, the arrangement and circuitry according to the invention ensures that, nevertheless, the corresponding photodectors 12d which are connected together in parallel are continuously illuminated. At the output of the electronic processing circuit 14 the signal −1 for X and 0 for Y would thus appear. In this way the location of the photodetector illuminated by the light ray 23 is clearly specified.

It is also conceivable that the fault of FIG. 4 is so formed that the laser beam is deflected as reflected ray 13' or 13" onto other neighbouring photodetectors. In any case the photodetectors illuminated by the light clearly show the angle at which the light incident thereon has left the surface 11 of the web 17. The closer the arrangement of the photodetectors 12 the more accurately can neighbouring narrow angular ranges be distinguished.

In practice for the monitoring of paper webs from 5 to 20 and preferably 10 individual Fresnel lenses are used per meter of the row.

It will be appreciated that the present teaching is not restricted to the manner in which the outputs of the individual photodetectors are combined as this can be done in a multitude of ways which will be readily apparent to the person skilled in the art. It is for example entirely possible, knowing the scanning speed of the laser beam, to associate, via suitable processing means, the position of the scanning bead at any one time with the outputs from the individual photodetectors. In this way not only will it be possible to detect the angle at which light rays leave the surface, and thus to assess the existence and nature of the fault, but also to determine the precise location of the fault.

It will also be readily understood that the row of Fresnel lenses taught by the present invention, if desired together with a corresponding array of photodetectors, could readily be used in conjunction with other optical monitoring apparatus and furthermore that a number of rows can be placed side by side to form an array. Although in the preferred embodiment herein disclosed the individual Fresnel lenses are cut into rectangles it is not strictly necessary that other than the adjacent side edges of neighbouring Fresnel lenses should be shaped so as to fit one against the other.

The adjacent side edges will preferably be made plane as used the preferred embodiment described above.

I claim:

1. Optical monitoring appratus for the separate detection of light rays which leave a surface scanned by a light beam at various angles in which there is provided, in the path of the light rays leaving the surface, a strip-like row of Fresnel lenses extending in the scanning direction, said strip like row comprising a series of individual Fresnel lenses arranged edge-wise directly adjacent one another with at least the adjacent edges of each neighbouring pair of Fresnel lenses being plane and their being further provided a respective group of a plurality of photodetectors arranged in the focal plane of each individual Fresnel lens and processing means for processing the electrical output signals from said photodetectors.

2. Optical monitoring apparatus according to claim 1 and in which said processing means comprises electrical circuit means interconnecting corresponding photodetectors of at least some of said groups for forming a common electrical output signal.

3. Optical monitoring apparatus according to claim 1 and in which the individual photodetectors of each group in the focal plane of the associated Fresnel lens are arranged in a rectangular coordinate system.

4. Optical monitoring apparatus according to claim 1 and in which from four to twelve individual photodetectors are arranged in each group.

5. Optical monitoring apparatus according to claim 1 and in which each of the individual photodetectors comprises a plurality of photoelectric inverters.

6. Optical monitoring apparatus according to claim 1 and in which said processing mens comprises electrical circuit means interconnecting the individual photodetectors for forming coordinate output signals characteristic of the angles at which said light rays leave said surface.

7. Optical monitoring apparatus according to claim 1 and in which each meter of the row contains from 5 to 20 individual Fresnel lenses arranged one after the other.

* * * * *